United States Patent
Moreau et al.

(10) Patent No.: US 8,924,171 B2
(45) Date of Patent: Dec. 30, 2014

(54) DEVICE FOR MONITORING THE STRUCTURE OF A VEHICLE

(75) Inventors: Katell Moreau, Paris (FR); Vincent Rouet, Orgeval (FR); Sébastien Rolet, Plaisance du Touch (FR)

(73) Assignee: European Aeronautic Defence and Space Company EADS France, Paris (FR)

(*) Notice: Subject to any disclaimer, the term of this patent is extended or adjusted under 35 U.S.C. 154(b) by 498 days.

(21) Appl. No.: 12/863,293

(22) PCT Filed: Mar. 18, 2009

(86) PCT No.: PCT/EP2009/002005
§ 371 (c)(1),
(2), (4) Date: Jul. 16, 2010

(87) PCT Pub. No.: WO2009/115315
PCT Pub. Date: Sep. 24, 2009

(65) Prior Publication Data
US 2011/0054813 A1    Mar. 3, 2011

(30) Foreign Application Priority Data
Mar. 20, 2008 (FR) ...................... 08 51819

(51) Int. Cl.
*G01N 27/90* (2006.01)
*G01R 31/00* (2006.01)
*G01N 33/00* (2006.01)

(52) U.S. Cl.
CPC .... *G01N 27/9006* (2013.01); *G01N 2033/0083* (2013.01)
USPC .......................................................... 702/59

(58) Field of Classification Search
CPC ....................................................... G01N 27/00
USPC ............................................................. 702/59
See application file for complete search history.

(56) References Cited

U.S. PATENT DOCUMENTS

2002/0027437 A1* 3/2002 Tasca ............................ 324/238
2002/0163333 A1* 11/2002 Schlicker et al. ............. 324/242
(Continued)

FOREIGN PATENT DOCUMENTS

EP           1 136 820        9/2001
EP           1 783 501        5/2007
(Continued)

OTHER PUBLICATIONS

Boyes, "Instrumentation Reference Book", Elsevier Butterworth-Heinemann (2002), 3rd edition, pp. 570-571.*

(Continued)

*Primary Examiner* — John Breene
*Assistant Examiner* — Yaritza H Perez Bermudez
(74) *Attorney, Agent, or Firm* — RatnerPrestia

(57) ABSTRACT

A device for monitoring the structure of a vehicle, including an electric measurement sensor, a processing circuit connected to the sensor for converting the sensor measurements into monitoring data, and a transmitter for transmitting the monitoring data to a collecting member, wherein the processing circuit is miniaturized and has a small size so as to be contained within a cube measuring 40×40×40 mm or less, is connected to the sensor by a short wired electrical connection, the length of which measures less than 200 mm, includes an onboard battery, and includes a radio means for transmitting the monitoring data to a mobile collecting member temporarily located in the vicinity thereof.

11 Claims, 5 Drawing Sheets

(56) References Cited

U.S. PATENT DOCUMENTS

| | | | |
|---|---|---|---|
| 2005/0203403 A1* | 9/2005 | Nakamura et al. | 600/447 |
| 2008/0288036 A1* | 11/2008 | Greenberg et al. | 607/115 |
| 2011/0112775 A1* | 5/2011 | Bramban | 702/56 |

FOREIGN PATENT DOCUMENTS

| | | |
|---|---|---|
| FR | 2 874 689 | 3/2006 |
| FR | 2 884 605 | 10/2006 |
| JP | 8203736 | 8/1996 |
| JP | 08203736 A * 8/1996 | H01F 17/00 |
| WO | WO 2006111679 A2 * 10/2006 | G01B 17/04 |

OTHER PUBLICATIONS

JP8203736A Machine Translation, printed from JPO on Jun. 14, 2012.*

JP8203736A Bibliographic Data, printed from Espacenet on Jun. 13, 2012.*

International Search Report dated Jun. 29, 2009.

* cited by examiner

| Examples of cases to be differentiated (not all cases are specified): | | | | | |
|---|---|---|---|---|---|
| Sensor (Ø = 20 mm) attached to the structure being tested | ◯ | ⊖ | ⊖ | ⊖ | ⊖— |
| State of the structure (crack state) | 0 | 1 | 4 | 6 | 8 |
| Maximum length of the crack (mm) | 0 | 2,5 | 10 | 15 | 20 |

$$T = T_n + \frac{T_n}{n}(cc\text{-}n)$$

DEVICE FOR MONITORING THE STRUCTURE OF A VEHICLE

FIELD OF THE INVENTION

The purpose of this invention is to monitor the state of metallic structures subjected to mechanical, vibratory and/or environmental stresses. It implements a methodology within an autonomous, onboard electronic system enabling cracks to be detected within these metallic structures in real time. The invention relates more particularly to the fields of air, sea and land transport.

BACKGROUND

The structures of means of transport, using the specific example of aircraft, are submitted to mechanical, environmental and/or vibratory stresses when in operation. These structures are inspected on a particularly regular basis so as to assess any emerging cracks: a short inspection is performed at each stop, and another, more in depth inspection is performed during maintenance operations referred to as C-check operations after 2,400 hours of flight. The latter inspections are long and costly as they require the removal of access panels to inspect the state of the metallic structures of the aircraft, which are inaccessible in normal time. Performed periodically, these inspections do not therefore enable cracks and their development to be continuously monitored. The same applies, in the railway sector, for some train parts, in particular for high-speed trains.

Systems for monitoring structures are developed in order to optimise and reduce these maintenance operations and therefore their costs and duration. For example, eddy current sensors are used to detect cracks appearing on metallic structures as illustrated in documents U.S. Pat. No. 6,952,095, GB-A-2 400 445 and GB-A-2 396 427.

In order to interpret the information transmitted by these sensors, several electronic interfaces have been produced. One of these interfaces interprets the impedance, more particularly the phase transmitted by the sensor. This interface is used to form a two-dimensional image of the surface to be inspected, as described in document U.S. Pat. No. 5,006,800. The disadvantages of this method include its bulk and high electricity consumption. Therefore, this method cannot be placed onboard, and the results from this method are not provided in real time.

Other interfaces interpret the conductivity transmitted by a sensor and are also used during maintenance operations. Crack monitoring cannot therefore be performed in a continuous manner.

Other systems, using acoustic sensors, have also been improved for studying, in a continuous manner, the state of the structures, as described in patent WO 2006 111679. These methods often consume large quantities of energy. The equipment must therefore be connected to the electrical network onboard the aircraft. Moreover, this equipment is very bulky.

Finally, onboard systems are known to list the number of stresses to which the aircraft is subjected, as described in document EP-A-1 018 641. These stresses: take-offs, landings, turbulences, pressures, etc. are listed by a system of logic gates and then recorded in a memory. Readings are then taken during maintenance operations, and thus help to guide operators during their inspections. However, these aforementioned methods do not provide direct information regarding the state of the structure.

SUMMARY

In the invention, the solution offered consists in using an autonomous, wireless transmission system, both battery-powered and above all small in size so as to be positioned where desired without any size restrictions, within a means of transport, that produces diagnostics regarding the state of the structure in real time. The method implemented by this autonomous system consists in analysing the signals transmitted by sensors via an onboard, electronic architecture combining analogue and digital circuits. With the processing algorithms being simplified, they can be placed onboard within a microcontroller, and the diagnostics can be performed in real time. The algorithms study in particular the impedance transmitted by the sensors and provides the state and development of cracks. Other functions determine the causes behind the emergence of cracks in addition to their development.

The advantages of using this system with respect to current systems include:
- a modular, electronic platform (interchangeable levels) enabling cracks and/or environmental stresses to be monitored,
- continuous monitoring of cracks using an autonomous, onboard electronic system with wireless communications, enabling improved monitoring of the development of the crack,
- more in-depth information regarding the emergence of cracks (the environmental data is recorded at the same time as the state of the structure),
- more in-depth information regarding the development of cracks (associated environmental data),
- real time information (in an immediate manner, without the use of post-processing operations via a PC) regarding the state of the structure (diagnostics), provided by the magnitude measurement,
- real time information regarding the state of the sensor (attached or not), provided by the phase measurement,
- easy collection of information via a radio connection,
- reduced costs and duration of maintenance operations, thus avoiding the removal of certain panels during unscheduled maintenance operations,
- low consumption of the equipment, enabling the latter to be used for a long period of time (target duration of 1 to 2 years),
- low equipment size (3D integration) so as to enable it to be positioned in areas with difficult access,
- an autonomous function, without requiring connection to the electrical network, thus easing its operation.

The invention therefore relates to a device for monitoring the structure of a vehicle, comprising an electric measurement sensor, a processing circuit connected to the sensor for converting the sensor measurements into monitoring data, and a transmission means for transmitting the monitoring data to a collecting member, characterised in that the processing circuit
- is miniaturised and has a small size so as to be contained within a cube measuring 40×40×40 mm or less,
- is connected to the sensor by a short wired electrical connection, the length of which measuring less than 200 mm,
- comprises an onboard battery,
- and comprises radio means for transmitting the monitoring data to a mobile collecting member temporarily located in the vicinity thereof.

The invention thus enables the restrictions presented in the systems previously described to be overcome, i.e.
- energy consumption,
- bulky equipment and therefore access restrictions,
- the presence of long wired connections (up to 50 m), the consultation and interpretation of data only performed during maintenance operations and not in real time, the discontinuous monitoring of the structures.

BRIEF DESCRIPTION OF THE DRAWINGS

The invention will be better understood after reading the following description and after examining the accompanying figures. These are presented as a rough guide and in no way as a limited guide to the invention. The figures show.

DETAILED DESCRIPTION

Figure 1A:
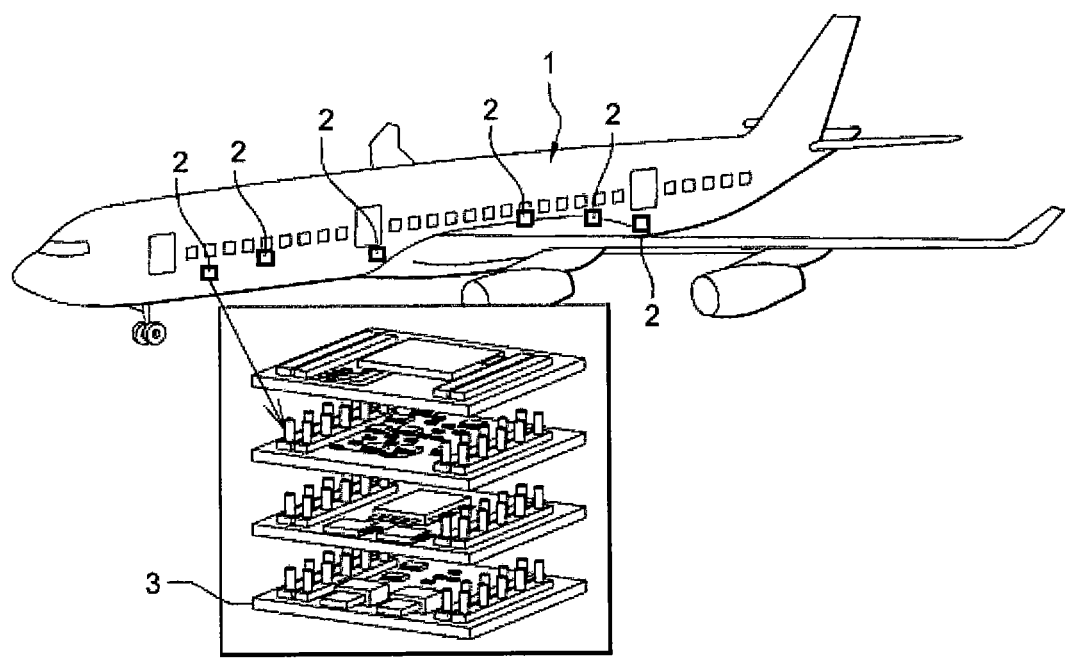
FIGS. 1a to 1c: a monitoring device according to the invention, different sensors and their installation within a particular vehicle.

FIG. 1a shows a means of transport 1, in this case an aircraft, with several onboard monitoring devices according to the invention, produced in the form of integrated electronic platforms or nodes. Each autonomous, wireless node, being small in size, is positioned in a location known to be sensitive. The set of platforms (sensor plus electronic circuit) monitors structure 1.

Figure 1B:
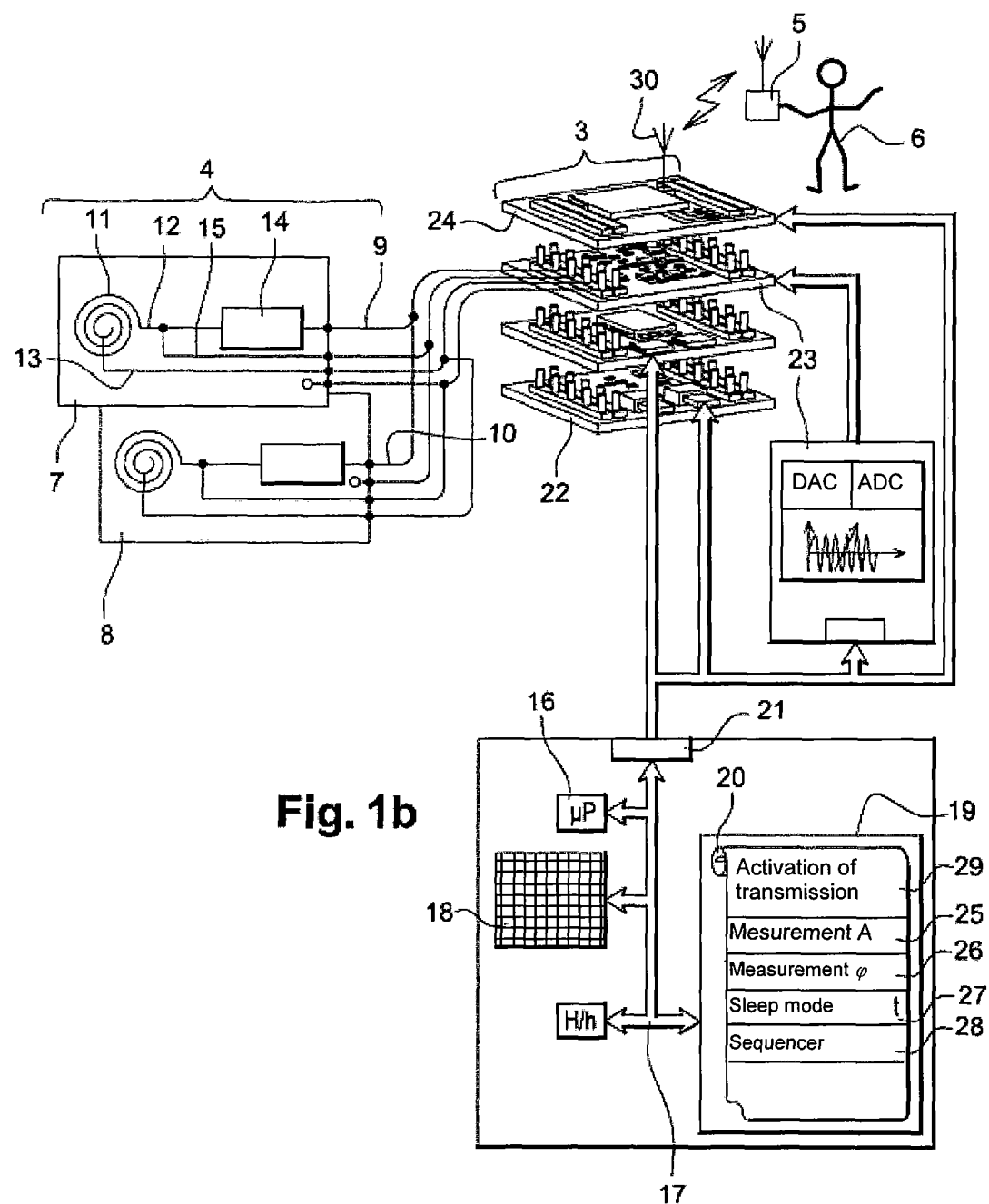

Each device comprises, FIG. 1b, a processing circuit 3 connected to a sensor 4. Circuit 3 converts the measurement signals produced by the sensor 4 into monitoring data. A collecting member 5, supported for example by an operator 6 passing in the vicinity of device 2 of structure 1, reads, when the vehicle is parked and preferably immobile, the monitoring data for maintenance purposes, for example in order to inspect the state of structure 1 or to incite the replacement of certain parts.

According to the invention, device 2 is miniaturised. In one example it comprises a processing circuit 3 with a size capable of being contained within a cube measuring 40 mm per side. An even larger level of miniaturisation is expected according to the development of electronic technology and more compact routing. This miniature device 2 also comprises a sensor 4. In one preferred example, sensor 4 is formed from a pair of two identical sensors 7 and 8, aimed at being positioned with one in the location of structure 1 being monitored and the other serving as a test sensor, positioned near to this location, in a location of structure 1 known to be healthy. The proximity of the two sensors is connected to the length of a wired electrical connection 9 and 10 connecting each sensor to circuit 3. In one example, flexible, double connections 9 and 10 have a length of between 50 mm and 200 mm. Connections 9 and 10 can be connected to sensors 7 and 8 and to circuit 3 in a definitive manner or via detachable connectors. In one example, connections 9 and 10 each support 4 wires. However, two sensors are not obligatory. Indeed, with the test sensor serving as a reference sensor, it can be omitted by providing, for example, onsite calibration or factory calibration of the measurement sensor response.

Figure 1C:
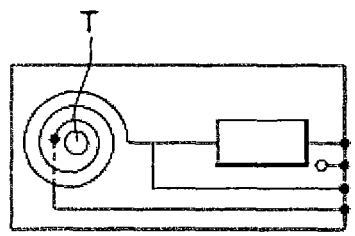

Each sensor is formed from a coil, preferably produced in this example from a spiral such as 11, engraved into a galvanised, flexible support, for example made out of a layer of double-sided galvanised polytetrafluoroethylene. With the support being double-sided, two connections 12 and 13, fitted on each side of the coil, or on the same side using a via, are connected to conductor strands of the wired connection 9. Connection 12 can include a resistor 14 for power matching. Connection 13 is preferably a ground connection, shared in particular between the two sensors 7 and 8 when two sensors are implemented. In another mode of embodiment, FIG. 1c, the sensor(s) have a hole T in their centre enabling them to be mounted around a rivet.

A connection 15, serving to transport the excitation signal and therefore measurement signal of the sensor, is connected at an intermediary point between coil 11 and resistor 14. The measurement principle is as follows: an alternating signal is produced by circuit 3 and, transported through the resistor 14, develops within structure 1 at the location where sensor 7 is positioned. If the structure is healthy, if there are no cracks, the magnitude of the signal will correspond to the presence of an induction coil and a resistor with known values. If, on the other hand, the area subjacent to coil 11 has split, if there is a crack, the circulation of the eddy currents is disrupted. Under these circumstances, the mutual inductance between the sensor and the source is reduced, whereas the resistance increases.

The presence of a test sensor 8 near to the measurement sensor 7 removes the need for calibration, while also making the effects from temperature irrelevant. The signals measured therefore involve a ratio or difference between the magnitudes of the signals measured by sensors 7 and 8 respectively. Moreover, if one of sensors 7 or 8 becomes detached from structure 1, the comparison of the measurement phase enables this to be detected immediately. Indeed, without mutual inductance with the structure for one of the sensors, the signals injected into sensors 7 and 8 are no longer synchronous, thus creating a phase discrepancy.

FIG. 1b represents the three-dimensional integration selected for circuit 3, in addition to the four different levels of nodes, with the unit forming a cube. Each level performs a particular function: radio transmission, conversion of the signals transmitted by the sensors into two proportional voltages, processing of the data by microcontroller and storing of the data in a memory, and autonomous power supply for the node and continuous voltage conversions (DC/DC) required to power the components located on each level. The levels are interchangeable and can be adapted according to the target application (for example mechanical and/or environmental stresses).

Circuit 3 thus comprises in a schematic manner and on one level, a microprocessor 16 connected by a data, address and control bus 17 to a memory 18, where monitoring data is stored, to a programme memory 19, recording a programme 20, to a clock H/h, capable of setting the microprocessor to operate in fast or slow mode and to a communications interface 21 capable of communicating between the first level and the other levels.

Interface 21 preferably comprises through connector pins for connecting the different levels of circuit 3 together. Therefore, the position of the latter can preferably be interchanged within the cubic circuit 3.

A second level 22 of circuit 3, also connected to interface 21, as to all of the other levels, is preferably a lower level in the sense that it is aimed at being the level accommodating the battery capable of operating between temperatures of −60° C. to +85° C., and that is attached to the structure not far from the structure being monitored.

A third level 23 communicates between the level of the microprocessor 16-20 and sensors 7 and 8 via connections 9 and 10. In this level 23, the electronic functions performed involve converting impedance into two proportional voltages, preferably in addition to the sinusoidal excitation of the injectors connected to the sensors.

A fourth level 24 acts as a radio connection with member 5.

In one preferred mode of embodiment, the different components (memory, sine wave generator, conditioning, radio) communicate via two types of serial interfaces: one preferred SPI (Serial Peripheral Interface) and a UART interface (Universal Asynchronous Receiver/Transmitter). Table 1 below displays the location of each function within the cube:

TABLE 1

| Function | Level number from 1 to 4 from the bottom upwards |
|---|---|
| Radio | 4 |
| Conditioning | 3 |
| Analogue-digital and digital-analogue conversions | 2 |
| Microcontroller | 2 |
| Memory (for example 1 Megabyte) | 2 |
| Power supply, voltage conversion | 1 |
| Sensors 7, 8 | external |

Tasks 25 to 29 are organised into sub-programmes within programme 20. Task 25 is a task measuring the magnitude of the signal transmitted by sensor 7 (and as required 8) so as to determine the length and depth of a crack. The measurement of the length of the crack will be explained at a later stage. Modifying the frequency of the signal injected by the injector also enables the depth of the crack in the metal to be determined. The higher the frequency, between 100 KHz and 1,000 KHz for example, the less the signal is able to penetrate the metal. Moreover, the response given by the sensor at different frequencies enables the depth of the crack to be determined.

Task 26 measures the phase φ between the signals from the two sensors and enables it to be determined whether the device remains in contact with structure 1.

Task 27 is a task causing processor 16 to enter into sleep mode. For example, over a period of several tens of minutes after taking a measurement, for example one hour, the microprocessor stops all functions. Preferably in this example, the microprocessor clock H/h passes from a fast rhythm H to a slow rhythm h so that counting the time of sleep mode does not disrupt the autonomous capacity of the device. With the aforementioned values, the duration of autonomy is estimated to equal approximately three years for easily available batteries. This autonomy must be compared to the excess consumption encountered in the prior art, which requires the use of additional power supply cables, which in turn add additional costs and add to the weight of the vehicle.

Task 28 represents the operating system, the sequencer of microprocessor 16.

Task 29 represents the operations launched when an operator 6 approaches circuit 2. The collection member 5 thus transmits, upon request from operator 6, an order, received by an antenna 30 of level 24, which itself transmits data stored in memory 18 to member 5.

A time interval between each measurement can be configured in task 27 via a PC, microcomputer interface. The measurements are then analysed by an algorithm 25-26 contained in circuit 3, and the state of the structure, represented with a number, is recorded in memory 18. The date associated with the measurement and produced by the clock H/h is also recorded. The diagnostics for the structure are thus immediately determined. The data is then recovered via radio on a personal digital assistant 5, PDA, or a mobile microcomputer. This data is displayed in a spreadsheet-type text editor, whenever required, in particular during each maintenance operation. The development of a crack is thus determined.

One additional function enables the environmental conditions to be determined simultaneously, and to be stored in the memory. Thus, by comparing this data (state of the structure and climatic data), the conditions of development of the crack are identified. Moreover, a critical level involving the length of the crack can be integrated into the system. An estimation of the date at which this length will be reached is automatically calculated by the algorithm. This calculation is based on linear regression using the dates recorded for each stage reached. Thus, maintenance can be scheduled or postponed, as required (after analysis of the length of the crack).

The invention will be used by airlines, shipping lines and railway operators to perform maintenance operations on their fleets (aircraft, helicopters, trains, boats, etc.). It determines at precisely what time a structure has become faulty (appearance of cracks) and the development of these faults. It therefore optimises maintenance operations: changing a part can be brought forward or postponed, thus avoiding unscheduled maintenance operations. Moreover, it limits the costs and duration of maintenance operations, as the user has to simply download the data and partially inspect the transport vehicle or aircraft. In addition, the monitoring operations for the development of cracks are improved and the causes of these cracks can be identified (change in temperature, pressure, humidity, take off, etc.).

Preferably, the set of sensors form a network and the nodes communicate with each other via a radio connection (for example a Zigbee-type connection in order to limit consumption). The data, analysed and recorded in a continuous manner, is collected on a regular basis by a data acquisition unit on the ground (for example every two or four months) by radio, during a maintenance operation on the aircraft. This data directly provides the state of the structure tested.

In order to limit the device's consumption, and given the average propagation time for a crack, for 100,000 hours of flight, the default value is set, in a preferential configuration, to one measurement per hour. When not taking this measurement, the device is in sleep mode. The data series obtained are processed by an algorithm in microcontroller 16-20, as soon as new measurements are obtained.

Figure 2:
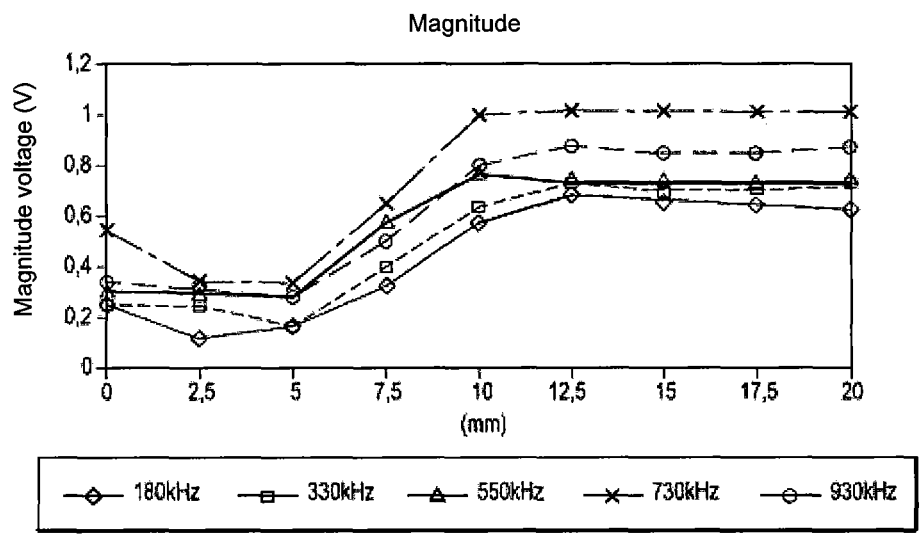
FIGS. 2 and 3: aspects of voltage plot diagrams respectively proportional to the magnitude and phase of a signal transmitted by a sensor of the invention.
Figure 3:
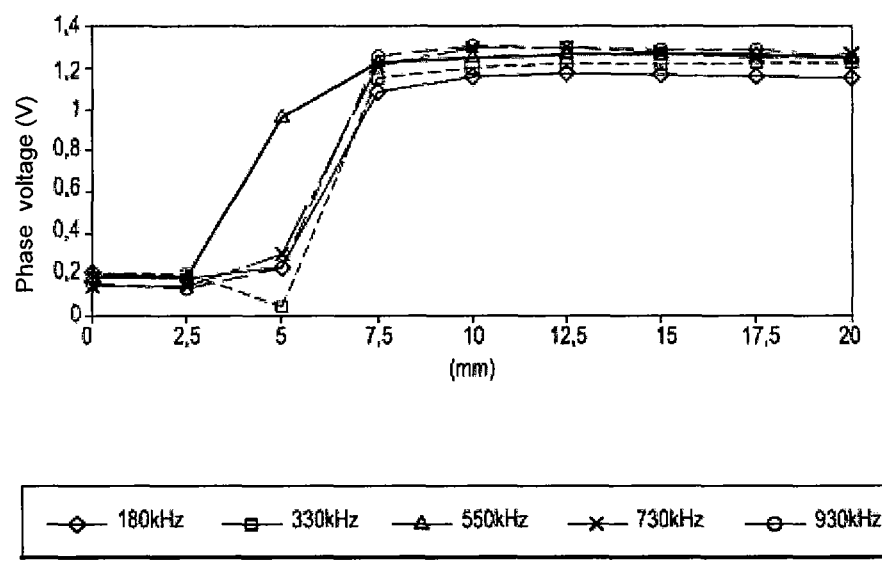
Figures 4, 5:
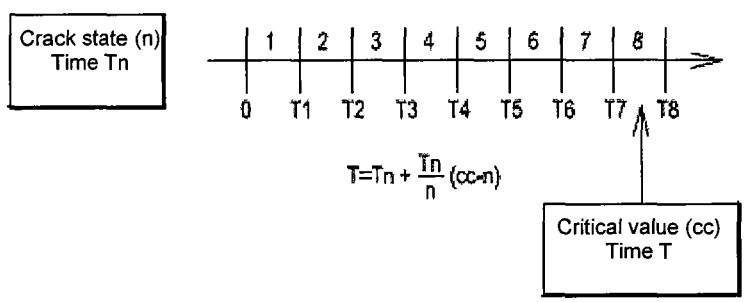
FIGS. 4 and 5: correspondences between the measurements taken by a sensor according to the invention and the size of a crack on the one hand and the date at which it will reach critical size on the other hand.
Figure 6:
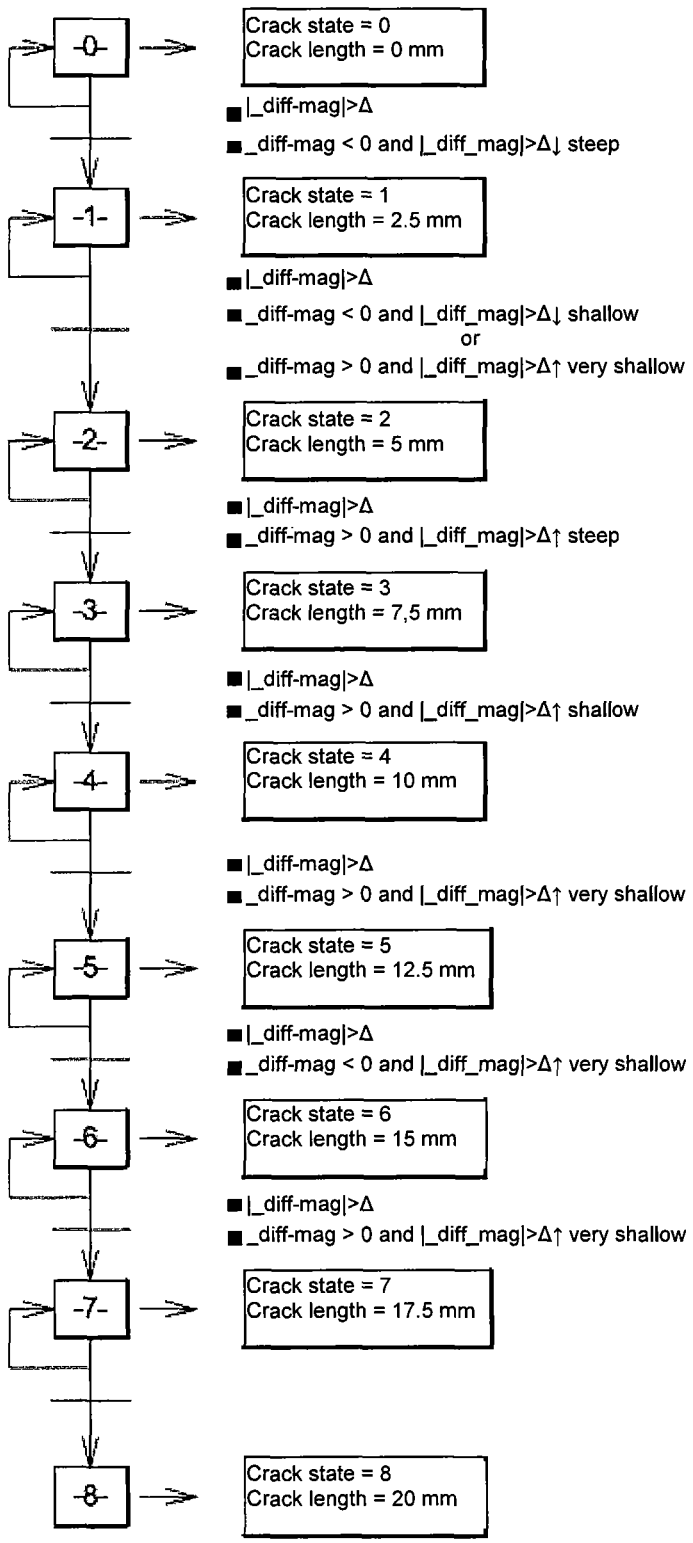
FIG. 6: one example of a crack monitoring algorithm implemented by the processing circuit of the invention.

FIGS. 2 and 3 present the characteristic outputs obtained after conditioning. The development of magnitude curves are firstly decreasing curves then increasing curves with more or less abrupt slopes according to the size of the crack detected. The algorithm presented in FIG. 6 is based on this slope. This algorithm determines the state of the structure (variable known as _crack_state), and therefore the length of the resulting crack, by stages, numbered in this example from 0 to 8.

The sensitive surface of the eddy current sensor is that of coil 11. In one preferred configuration, this involves a circle with a diameter equal to 20 mm. This size limits the maximum length of the crack being detected. The number of different stages is also fixed by the diameter of the sensitive surface. In this example, the sensitive surface has been subdivided into 8 parts, i.e. lengths of 2.5 mm. The algorithm described in FIG. 6 can easily be adapted to suit other sensitive surfaces and for a number of different stages.

Table 2 below describes the slopes of the voltage characterising the magnitude.

TABLE 2

| Stage | Positive slope (↑) | Negative slope (↓) | Slope (+++: steep; ++: shallow; +: very shallow) |
|---|---|---|---|
| 1 | | | +++ |
| 2 | | | ++ |
| 3 | X | | +++ |
| 4 | X | | ++ |
| 5 | x | | + |
| 6 | | X | + |
| 7 | x | | + |
| 8 | | x | + |

The algorithm mainly uses the magnitude of the impedance imbalance of the bridge formed by the two sensors 7 and 8. For example, a difference of 100 mV at 180 KHz reveals a crack with a length of 5 mm. The phase is used in this example to determine whether the sensor is correctly attached to the structure. The first measurement is taken on a healthy structure, i.e. without any cracks to act as a reference measurement. The two voltages caused by these measurements are stored is variables Mag_n and Phase_n at time n. For the following measurements, the previous measurements are stored in variables characterising the time n−1, Mag_n−1 and Phase_n−1. The new values are stored in variables relating to time n. The algorithm works on the difference in magnitude of these two values (dif_mag), i.e. on the signal and the difference between the latter. According to the positive signal (Δ↑) or negative signal (Δ↓), and the more or less abrupt slope (steep, shallow or very shallow) of this difference, the state characterising the structure develops within the different stages numbered from 0 to 8 as presented by the algorithm. The monitoring operation in time thus proposed by the algorithm in FIG. 6 takes into account the fact that, for a given crack, the signal originally begins by decreasing before increasing, thus with conflicting variations.

For example, in order to pass from state 0 to state 1, the difference in magnitude must be more than a fixed, steep Δ↓ limit.

The level of precision of the measurement is approximately equal to 50 mV, explaining why the difference in magnitude measured between the two sensors, equal to less than 50 mV (referred to as A in the algorithm), will not be taken into account by the latter. If the sensor is improperly attached to the structure, i.e. if the phase and magnitude values exceed a fixed limit, a warning message is automatically recorded.

The algorithm thus analyses the state of the structure in real time and then records the value of this state in memory. The maximum length of the crack is thus obtained. The time associated with this measurement is also recorded, which enables the development of the crack to be monitored in detail.

The device also includes a function for obtaining environmental parameters (temperature, humidity), in addition to parameters related to pressure and vibrations. This function is activated if the user desires to compare the different states of the structure tested with the environmental parameters recorded. Thus, the conditions involved in the emergence and development of cracks can be identified.

The invention claimed is:

1. A device for monitoring the structure of a vehicle, comprising:
   an electric measurement sensor,
   a processing circuit connected to the sensor for converting the sensor measurements into monitoring data, and
   a transmission means for transmitting the monitoring data to a collecting member,
   wherein the processing circuit;
   is organized according to a multi-level architecture each level of the processing circuit connected to each other level with an interface including connector pins for connecting the different levels of circuit, wherein the processing circuit
   is miniaturised so as to be contained within a cube measuring 40×40×40 mm or less, and
   is connected to the sensor by a short wired electrical connection, the length of which is less than 200 mm, and
   wherein the processing circuit includes:
   a first level including an electrical power supply comprising an onboard battery,
   a second level including digital processing circuitry, the second level being positioned below the first level in the multi-level architecture,
   a third level, positioned below the second level in the multi-level architecture, for converting each measurement signal transmitted by the sensors into two proportional voltages, wherein the circuitry on the second level converts the two proportional voltages into digital values,
   a fourth level, positioned below the third level in the multi-level architecture, including a network radio means of a Zigbee-type for transmitting the monitoring data to a mobile collecting member temporarily located in a vicinity of the device,
   wherein the sensor is an eddy current sensor and comprises a first measurement sensor positioned on the structure in a location to be monitored, and a second test sensor, identical to the first measurement sensor, and positioned on the structure in a healthy location in order to measure adhesion of the two sensors to the structure being monitored by a difference in phase between the signals produced by the two sensors.

2. A device according to claim 1, wherein the processing circuit comprises a sensor transmitting function which is activated by the collecting member when the vehicle is parked and immobile.

3. A device according to claim 1, wherein the sensor is a crack measuring sensor.

4. A device according to claim 1, wherein the eddy current sensor is a spiral coil supported by a flexible circuit galvanised on both sides and connected to the processing circuit via a double flexible wired connection; positioned in a location being monitored and associated with another reference sensor mounted near to the location being monitored in a location known to be healthy, and in that the processing circuit measures the difference in the signal transmitted by one sensor when compared to the other.

5. A device according to claim 1, wherein the eddy current sensor has a given surface size and in that the processing circuit comprises means for quantifying the measurements so as to measure development of a size of a crack.

6. A device according to claim 1, wherein the processing circuit comprises a memory to record at least one of the measurements or monitoring data.

7. A device according to claim 1, wherein the processing circuit is a low consumption circuit and thus comprises a sequencer to perform measurements at intervals of several tens of minutes and to cause the circuit to enter into sleep mode between consecutive measurements.

8. A device according to claim 1, wherein the processing circuit comprises a battery capable of operating between temperatures from −60° C. to +85° C.

9. A device according to claim 1, wherein the processing circuit comprises a circuit for measuring a date in order to record this date in connection with a measurement, and a programe for deducing development of a crack despite conflicting variations in the measurement signal.

10. A device according to claim 1, wherein the processing circuit comprises a sinusoidal signal generator with a frequency of between 100 KHz and 1,000 Khz for measuring a depth of the crack, and a sequencer for varying the frequency during a measurement so as to explore the depth of the crack.

11. A device according to claim 1, wherein the sensor has a hole in its centre so as to be positioned around a rivet.

* * * * *